United States Patent [19]

Kress et al.

[11] Patent Number: 5,068,335

[45] Date of Patent: Nov. 26, 1991

[54] PROCESS FOR THE PREPARATION OF 4-HYDROXY-2,2,6,6-TETRAMETHYL-PIPERIDINE

[75] Inventors: Ulrich Kress, Bensheim/Bergstrasse; Rudolf Maul, Lorsch/Hessen; Siegfried Kintopf, Bensheim/Bergstrasse, all of Fed. Rep. of Germany

[73] Assignee: Ciba-Geigy Corporation, Ardsley, N.Y.

[21] Appl. No.: 539,298

[22] Filed: Jun. 18, 1990

Related U.S. Application Data

[63] Continuation of Ser. No. 434,539, Nov. 8, 1989, abandoned, which is a continuation of Ser. No. 186,837, Apr. 27, 1988, abandoned.

[30] Foreign Application Priority Data

May 5, 1987 [CH] Switzerland ............... 1707/87

[51] Int. Cl.$^5$ ............................................. C07D 211/46
[52] U.S. Cl. ........................................................ 546/242
[58] Field of Search ........................................... 546/242

[56] References Cited

U.S. PATENT DOCUMENTS

| | | | |
|---|---|---|---|
| 4,076,946 | 2/1978 | Miller | 560/78 |
| 4,208,525 | 6/1980 | Rasberger et al. | 546/184 |
| 4,650,899 | 3/1987 | Kervennal et al. | 560/359 |
| 4,731,448 | 3/1988 | Issler et al. | 546/248 |

FOREIGN PATENT DOCUMENTS

| | | |
|---|---|---|
| 0000805 | 2/1979 | European Pat. Off. |
| 002308 | 6/1979 | European Pat. Off. |
| 2656763 | 6/1977 | Fed. Rep. of Germany |
| 2656764 | 7/1977 | Fed. Rep. of Germany |
| 2656765 | 7/1977 | Fed. Rep. of Germany |
| 602644 | 7/1978 | Switzerland |

OTHER PUBLICATIONS

J. Org. Chem., 27, 1695-1703 (1962).
CA 68(1968), 114390m, R. Briere, Commis. Energ. AT. (FR) Rapp. No. 3175, 105pp. (1967).
J. Org. Chem., 22, 1061-1065, (1957). E. Malley, et al.
CA 60 (1964), 2881d [L. Zhelyazkov, et al. Farmatsiya (Sofia) 13(3), 11-17 (1963)].
Helv. Chim. Acta 49 (1966), 690-695.
C. A. 101 (1984), 90186w [V. Konyukhov, et al., Kinet. Katal. 1984, 25(3), 578-82].
C. A. 101, 6996e (1984) [T. Tsar'kova, et al., Elektrokhimiya 1984, 20(3), 404-7].
Herbert O. Hoise, Modern Synthetic Reactions 2nd Ed., W. A. Benjamin, Menlo Park, CA 1972, p. 9.

Primary Examiner—John M. Ford
Attorney, Agent, or Firm—Harry Falber

[57] ABSTRACT

A process for the preparation of 4-hydroxy-2,2,6,6-tetramethyliperidine (HTMP) by hydrogenation of triacetonamine (TAA) in the presence of an Ni, Co, Ru, Rh, Os or Ir hydrogenation catalyst is described. The process is carried out in the melt without a solvent.

9 Claims, No Drawings

PROCESS FOR THE PREPARATION OF 4-HYDROXY-2,2,6,6-TETRAMETHYLPIPERIDINE

This application is a continuation of application Ser. No. 434,539, filed 11/8/89, which is a continuation of Ser. No. 186,837. filed 4/27/88, now abandoned.

The present invention relates to a process for the preparation of 4-hydroxy-2,2,6,6-tetramethylpiperidine by catalyst hydrogenation of 4-oxo-2,2,6,6-tetramethylpiperidine (=triacetonamine).

4-Hydroxy-2,2,6,6-tetramethylpiperidine (abbreviated to HTMP below) is a large-scale industrial intermediate product which is required for the preparation of high-quality light stabilizers from the class of hindered amines (2,2,6,6-tetramethylpiperidines). There is great interest in preparing this intermediate product in the maximum possible purity and by processes which are optimum from the economic and ecological standpoint.

HTMP is prepared practically exclusively by reduction of triacetonamine (abbreviated to TAA below). A large number of publications relating to such reduction processes exist. Thus, J.Org.Chem. 27 (1962), 1695-1703 describes the reduction with sodium borohydride, and Commis.Energ.At. (Fr.), Rapp. No. 3175, 105 pp (1967) abstracted in C.A. 68 (1968), 114390m, describes the reduction with lithium aluminium hydride. The most advantageous and industrially most useful reduction method, however, is catalytic hydrogenation of TAA. This hydrogenation is carried out in the presence of various noble metal catalysts and in a solvent, for example in ethanol or other alcohols [J.Org.Chem. 22 (1957), 1061-1065; Farmatsiya 13 (3), 11-17 (1963), abstracted in Heterocyclic Compounds, Volume 37 (1964), 2881d; and Helv.Chim.Acta 49 (1966), 690-695]. The reduction in alcohols was for a long time the most common method of preparation. DE-A-2656763 proposes tertiary aliphatic phosphoric acid esters and DE-A-2656765 proposes organic solvents containing no hydroxyl groups, such as hydrocarbons (for example toluene or xylene) or ethers (for example petroleum ether, dibutyl ether or mesitylene) as the reaction medium. Finally, DE-A-2656764 and CH-A-602644 describe the hydrogenation of TAA in an aqueous medium. The latter method has been used to date in the large-scale industrial preparation of HTMP. The use of organic solvents has the disadvantage that expensive recovery operations for the solvent must be accepted as the price and that their use presents problems from the ecological and process technology standpoint. Although these disadvantages are avoided by the aqueous process, the yield which can be achieved is lower because of the occurrence of side reactions. There is also the problem of the process effluent.

It has now been found, surprisingly, that hydrogenation of TAA can be achieved with certain catalysts even without the use of a solvent, and that not only can the disadvantages described above thereby be prevented, but that such a procedure even provides further advantages.

The process according to the invention for the preparation of HTMP by catalytic hydrogenation of TAA in the presence of a metal catalyst from the group comprising Ni, Co, Ru, Rh, Os and Ir catalysts or mixtures thereof comprises carrying out the hydrogenation in the melt without using a solvent.

The metal catalysts (hydrogenation catalysts) which can be used in the process according to the invention are advantageously employed in the forms customary for this purpose, that is to say the particular metal is applied to a support, for example to active charcoal, kieselguhr, aluminium oxide, barium sulfate and the like. The catalysts can be activated with further metals, for example with Mg, Zr or Mo. Ni catalysts, for example in particular Raney nickel, and also Rupe nickel, Urushibara nickel or nickel on other of the abovementioned supports, are preferably used in the process according to the invention, and Ru catalysts, for example ruthenium on active charcoal, ruthenium black, ruthenium on kieselguhr or ruthenium on other supports, such as aluminium oxide or barium sulfate, are used in particular.

The catalyst is fully recyclable in the process according to the invention. It is surprising that in spite of the absence of a solvent, the product melt can be separated off completely and without problems. If the process is carried out batchwise, the catalyst is advantageously removed by filtration, sinter metal plugs (sinter metal cartridges), for example with a pore diameter of 3 μm to 25 μm, being particularly advantageously used for this. For further purification, the catalyst can be rinsed with fresh TAA melt, before it is reused in a subsequent batch.

If the process is carried out continuously, filtration of the catalyst is dispensed with. In this case, a fixed bed catalyst, for example a high pressure fixed bed hydrogenation unit, is particularly advantageously used. The product melt is in this case removed continuously and fresh TAA melt is fed in.

In the batch process, the catalyst is used in an amount of, for example, 0.05-2%, preferably 0.1-1.5% and in particular 0.25-1%, based on the TAA employed.

The hydrogenation is advantageously carried out at temperatures from 60° to 180° C., for example 60° to 150° C. and preferably 80° to 150° C. In the batchwise procedure, the hydrogenation is preferably started at a low temperature, for example 60° C., preferably at 70°-90° C. and in particular at about 80° C. The temperature then increases and is advantageously kept constant in a temperature range of 100°-180° C., for example 100°-150° C., in particular 120°-140° C., preferably 125°-135° C. and above all in the region of about 130° C., during the hydrogenation. In the case of the continuous procedure, it is advantageous to start the hydrogenation at lower temperatures when the hydrogenation unit is started up. The abovementioned preferred temperature ranges are used in continuous operation.

The hydrogen pressure during the hydrogenation can be, for example, in the range from 10 to 250 bar, for example 10 to 200 bar, in particular 20 to 200 bar. The hydrogen pressure applied chiefly depends on the hydrogenation unit available. In the batchwise procedure, hydrogen pressures of 20-100 bar, for example 30-80 bar, are advantageous. However, pressures of 100-250 bar, for example 150-200 bar, can also advantageously be used in high pressure units. The latter pressures are particularly customary with a continuous procedure in high pressure fixed bed hydrogenation units. The hydrogenation time can vary within wide limits and depends on the catalyst used, the hydrogen pressure, the reaction temperature and the unit used. It can last, for example, from 30 seconds to 2 hours, in particular 1 minute to 1 hour, for example 1 to 30 minutes. In the continuous procedure, for example, residence times of 1 to 60 minutes, in particular 10 to 30 minutes, are to be expected in practice. The reaction times, like the amount of $H_2$ required, also depend on the quality of the TAA used, that is to say on its purity. Less pure TAA increases the hydrogenation time and the $H_2$ consumption accordingly.

As already mentioned, the process according to the invention can be carried out batchwise or continuously. Preferred reaction conditions for these two procedures are given above. In the case of the continuous procedure, a catalyst fixed bed is particularly advantageously used.

Hydrogenations in the melt are known in principle for other types of reactions, for example the hydrogenation of nitro compounds, carboxylic acids and the like, see EP-A-2308, EP-A-805, US-A-4,076,946 and Kinet. Katal. 1984, 25 (3), 578-82, abstracted in C.A. 101 (1984), 90186w. However, it was not to be expected that the hydrogenation of TAA, which has been the subject of intensive attempts to improve the process for a long time, takes place smoothly in the melt, that many disadvantages of the known reduction processes can be avoided and that significant advantages can even be achieved by the procedure in the melt.

Of the particular advantages of the process according to the invention over the known solvent processes, the following—apart from the avoidance of solvent regeneration and effluent problems—may be mentioned as examples: considerably increased space-time yield, shorter reaction times, fewer side reactions, very pure product, high absolute yields, increased selectivity and no additional purification operations before further use of the HTMP obtained.

The advantage last mentioned is important, for example, if the HTMP is used for the preparation of 1-(2-hydroxyethyl)-4-hydroxy-2,2,6,6-tetramethylpiperidine (HE-HTMP). For this purposes, HTMP is reacted with ethylene oxide. The intermediate isolation or purification of the HTMP which is otherwise necessary is dispensed with if the melt hydrogenation of TAA, according to the invention is used. The process described in European Patent Application No. 86810554.5 can advantageously be used for the preparation of HE-HTMP, concentration of the crude HTMP solution being omitted, since a pure HTMP melt is already obtained by the process according to the invention.

The following examples further illustrate the process according to the invention. As in the remainder of the description, parts and percentage data therein relate to the weight, unless indicated otherwise.

EXAMPLES 1-5

100 g of distilled TAA (purity: 99%) and 1 g of 5% strength ruthenium on active charcoal (Ru/C) are introduced into a 300 ml hydrogenation autoclave. After flushing the apparatus with $H_2$, the desired hydrogen pressure is established and the hydrogenation is started at 80° C. The temperature rises rapidly to 130° C. and is then kept constant. When the uptake of $H_2$ has ended, the catalyst is filtered off at 150° C. over a sinter metal cartridge (pore size 7-15 μm) from the bottom valve. The catalyst is reused for the next batch, if appropriate after rinsing with pure TAA melt. The filtered HTMP melt is weighed and analyzed by gas chromatography. The following table shows the resulting analytical values, the uptake of hydrogen and the hydrogenation time, for some batches under various $H_2$ pressures.

TABLE

| Example | $H_2$ pressure (bar) | Hydrogenation time (min.) | Uptake of $H_2$ (% of theory) | TAA conversion to HTMP (in % by weight) | HTMP in the melt (in % by weight) |
|---|---|---|---|---|---|
| 1 | 20 | 28 | 100 | 99.6 | 98.2 |
| 2 | 40 | 15 | 110 | 96.4 | 96.7 |
| 3 | 100 | 7 | 101 | 99.9 | >99 |
| 4 | 100 | 2 | 99 | 99.9 | >99 |
| 5 | 200 | 1 | 100 | 99.9 | >99 |

EXAMPLE 6

Continuous hydrogenation: TAA melt is pumped by means of a heated pump at 70°-80° C. into a high pressure fixed bed hydrogenation unit (volume: 500 ml) containing 150 ml of Ru/C catalyst in bulk. The entire apparatus is under an $H_2$ pressure of 150-200 bar and is kept at a temperature of 130° C. After a residence time of 10 to 30 minutes, the HTMP melt leaves the reactor and is analyzed by gas chromatography. A TAA conversion to HTMP of about 99.9% by weight is achieved, and the content of HTMP in the product melt is >99%.

We claim:

1. A process for the preparation of 4-hydroxy-2,2,6,6-tetramethylpiperidine by catalytic hydrogenation of 4-oxo-2,2,6,6-tetramethylpiperidine in the presence of a metal catalyst from the group consisting of Ni, Co, Ru, Rh, Os and Ir catalysts or mixtures thereof, which comprises carrying out the hydrogenation in the melt without using a solvent.

2. The process according to claim 1, wherein an Ni or Ru catalyst is used as the catalyst.

3. The process according to claim 1, wherein the hydrogenation is carried out at temperatures from 60° to 180° C.

4. The process according to claim 1, wherein the hydrogenation is carried out under a hydrogen pressure of 10 to 250 bar.

5. The process according to claim 1, wherein a batchwise procedure is followed.

6. The process according to claim 5, wherein the hydrogenation is carried out under a hydrogen pressure of 20-100 bar.

7. The process according to claim 1, wherein the procedure is continuous.

8. The process according to claim 7, wherein the catalyst is in the form of a fixed bed.

9. The process according to claim 7, wherein the hydrogenation is carried out under a hydrogen pressure of 150-200 bar.

* * * * *